US007864974B2

(12) United States Patent
Chen

(10) Patent No.: US 7,864,974 B2
(45) Date of Patent: Jan. 4, 2011

(54) EARPHONE DEVICE INTEGRATED WITH MICROPHONE

(76) Inventor: Lu-Cheng Chen, 2F, No. 22, Lane 76, Sec. 7, Hsin Hai Rd., Wen Shan Dist., Taipei City (TW)

( * ) Notice: Subject to any disclaimer, the term of this patent is extended or adjusted under 35 U.S.C. 154(b) by 1213 days.

(21) Appl. No.: 11/168,518

(22) Filed: Jun. 29, 2005

(65) Prior Publication Data

US 2007/0003094 A1 Jan. 4, 2007

(51) Int. Cl.

| | |
|---|---|
| ***H04R 1/02*** | (2006.01) |
| *H04R 25/00* | (2006.01) |
| *H04R 25/02* | (2006.01) |
| *A61B 7/02* | (2006.01) |

(52) U.S. Cl. ........................ 381/345; 381/326; 381/328; 381/375; 181/130; 181/132; 181/135

(58) Field of Classification Search ................... 381/74, 381/375

See application file for complete search history.

(56) References Cited

U.S. PATENT DOCUMENTS

| | | | | |
|---|---|---|---|---|
| 4,807,612 | A * | 2/1989 | Carlson | 128/868 |
| 5,420,935 | A * | 5/1995 | Shinohara et al. | 381/370 |
| 5,631,965 | A * | 5/1997 | Chang et al. | 381/72 |
| 6,381,337 | B1 * | 4/2002 | Greenberg | 381/345 |
| 2003/0202668 | A1 * | 10/2003 | Kao | 381/74 |

* cited by examiner

*Primary Examiner*—Brian Ensey
*Assistant Examiner*—Sunita Joshi
(74) *Attorney, Agent, or Firm*—Rosenberg, Klein & Lee

(57) ABSTRACT

An earphone device integrated with a microphone has a main body, a microphone unit and a speaker unit. The microphone unit has a sound-absorbing film and a circuit unit, the sound-absorbing film being a hollow column and being connected to the main body through a rear end thereof, and the circuit unit being fixed on the main body and electrically connected to the sound-absorbing film. The speaker unit is mounted inside the sound-absorbing film of the microphone unit such that the microphone unit is located peripheral to the speaker unit. A microphone and an earphone can thus be integrated together as a whole so as to form an earphone device that can be used conveniently.

10 Claims, 4 Drawing Sheets

EARPHONE DEVICE INTEGRATED WITH MICROPHONE

BACKGROUND OF THE INVENTION

1. Field of the Invention

The present invention is related to an earphone device integrated with a microphone, and more particularly to an earphone device in which a microphone and an earphone are integrated together for facilitating use thereof.

2. Description of Related Art

Use of an earphone to receive sound input is common. Activities such as listening to music on an airplane, or using a Walkman, radio or mobile phone are conducted with the use of earphones. Moreover, some earphones are combined with a microphone, in applications such as the hands-free device for a mobile phone.

Reference is made to FIG. 1. A conventional hands-free device includes an earphone 90 and a microphone 91, which are independent of each other. In the device, after the earphone 90 and the microphone 91 are connected to the mobile phone 93 through a signal line 91, the electronic signals from the mobile phone 93 can be converted into sound, which can be heard by human ears. The user can hear the sound by plugging the earphone into the ear. Additionally, the microphone 91 is approximately positioned around the mouth of the user to pick up the voice of the user; the voice can then be converted into electronic signals and transmitted to the mobile phone 93.

However, the conventional earphone and microphone are independent of each other, and thus must be placed in different positions during use. This is unavoidably inconvenient for assembly. In particular, when using the microphone, if the microphone is not fixed, it is easily shaken, which is unfavorable for voice reception.

Although the conventional microphone has developed to be clipped on the clothing of the user with a clip, this clipping manner causes a complex structure and also an increased cost. Further, the exposed microphone also influences the user's appearance, and hinders the activity of the user due to accidental contact. Therefore, it is quite inconvenient.

SUMMARY OF THE INVENTION

The main object of the present invention is to provide an earphone device integrated with a microphone, in which the microphone and the earphone are integrated together for facilitating use thereof, to provide convenient microphone assembly without shaking, to receive a user's voice, to simplify the whole structure thereof, and to reduce the cost thereof. Further, the microphone is not exposed.

For achieving the above objects, the present invention provides an earphone device integrated with a microphone including a main body, a microphone unit connected to the main body, and a speaker unit mounted inside the microphone.

According to the present invention, the microphone unit is integrated in the earphone device such that the earphone device may concurrently have the functions of earphone and microphone. While in use, the earphone and the microphone are fixedly assembled in the same position, together, so that the assembly is more convenient and the microphone is more stable, which facilitates sound reception. Furthermore, the microphone does not need a clip to clip onto the clothing worn by the user, so the whole structure can be simplified and the manufacturing cost can be reduced. Moreover, the microphone is plugged into the ear canal of the user together with the earphone device, so it is not exposed, and thus, the user's appearance will not be influenced and the activity of the user will not be hindered, either.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF PREFERRED EMBODIMENTS

Figure 1:
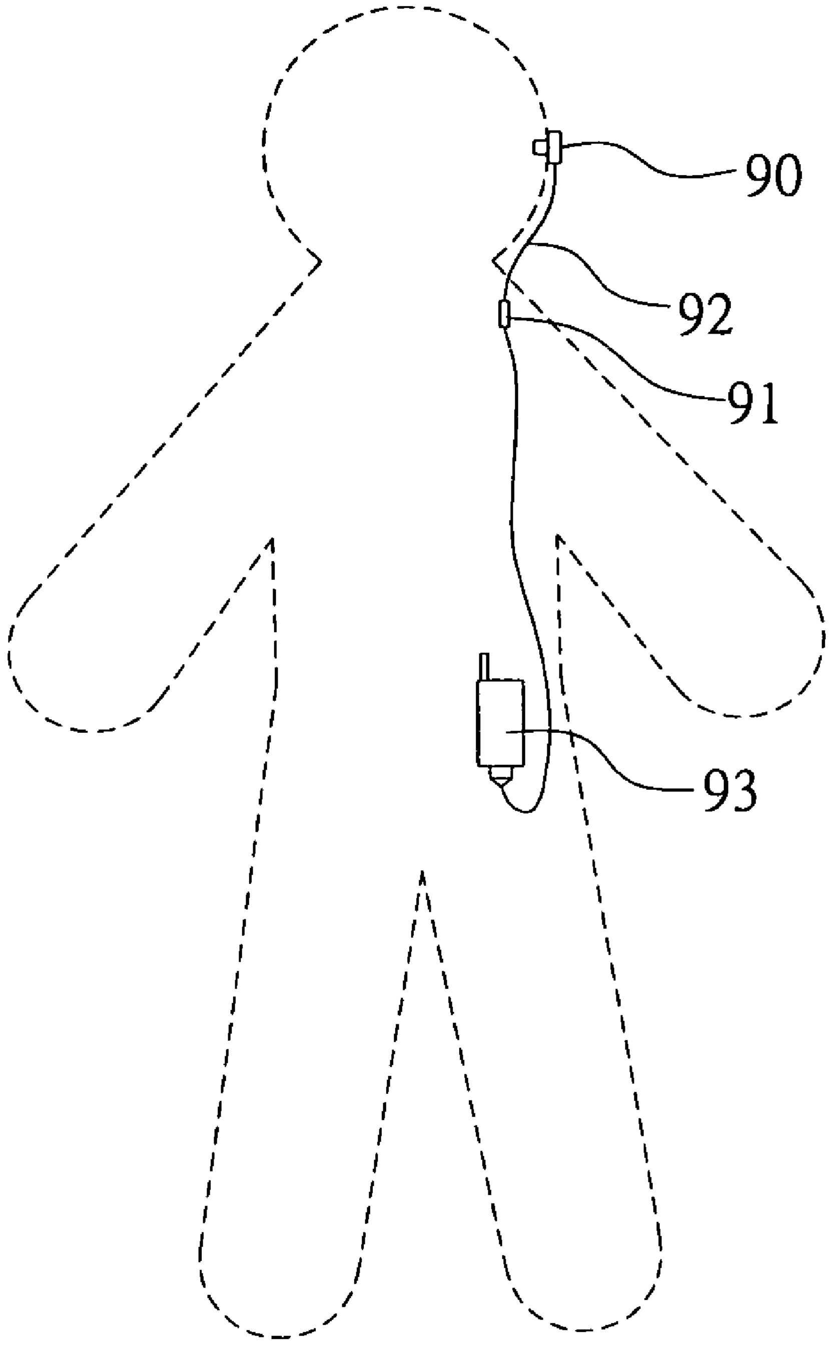
FIG. 1 PRIOR ART
FIG. 1 is a schematic view showing the states of the conventional earphone and microphone.
Figure 2:
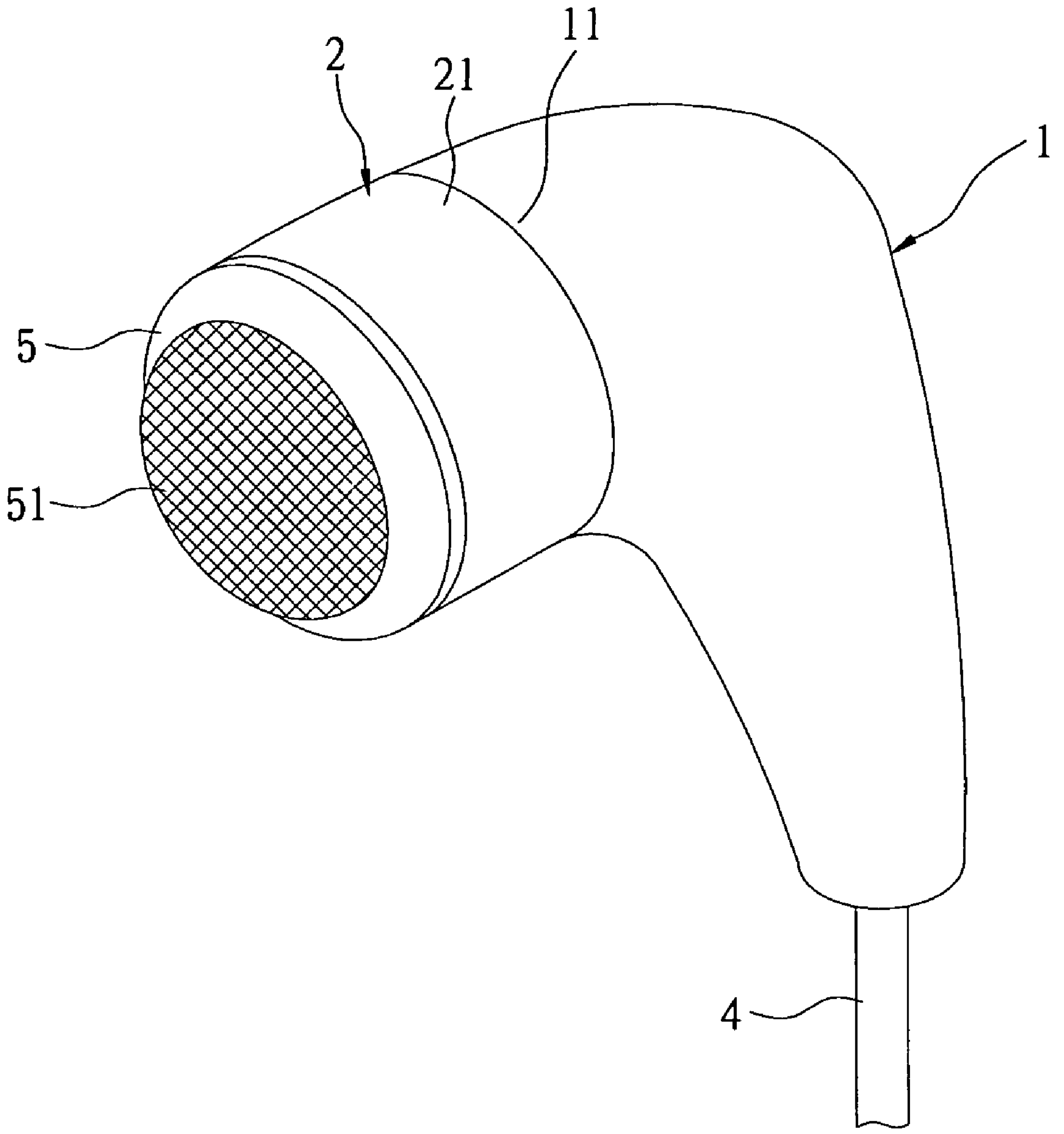
FIG. 2 is a 3D schematic view showing an earphone device according to the present invention.
Figure 3:
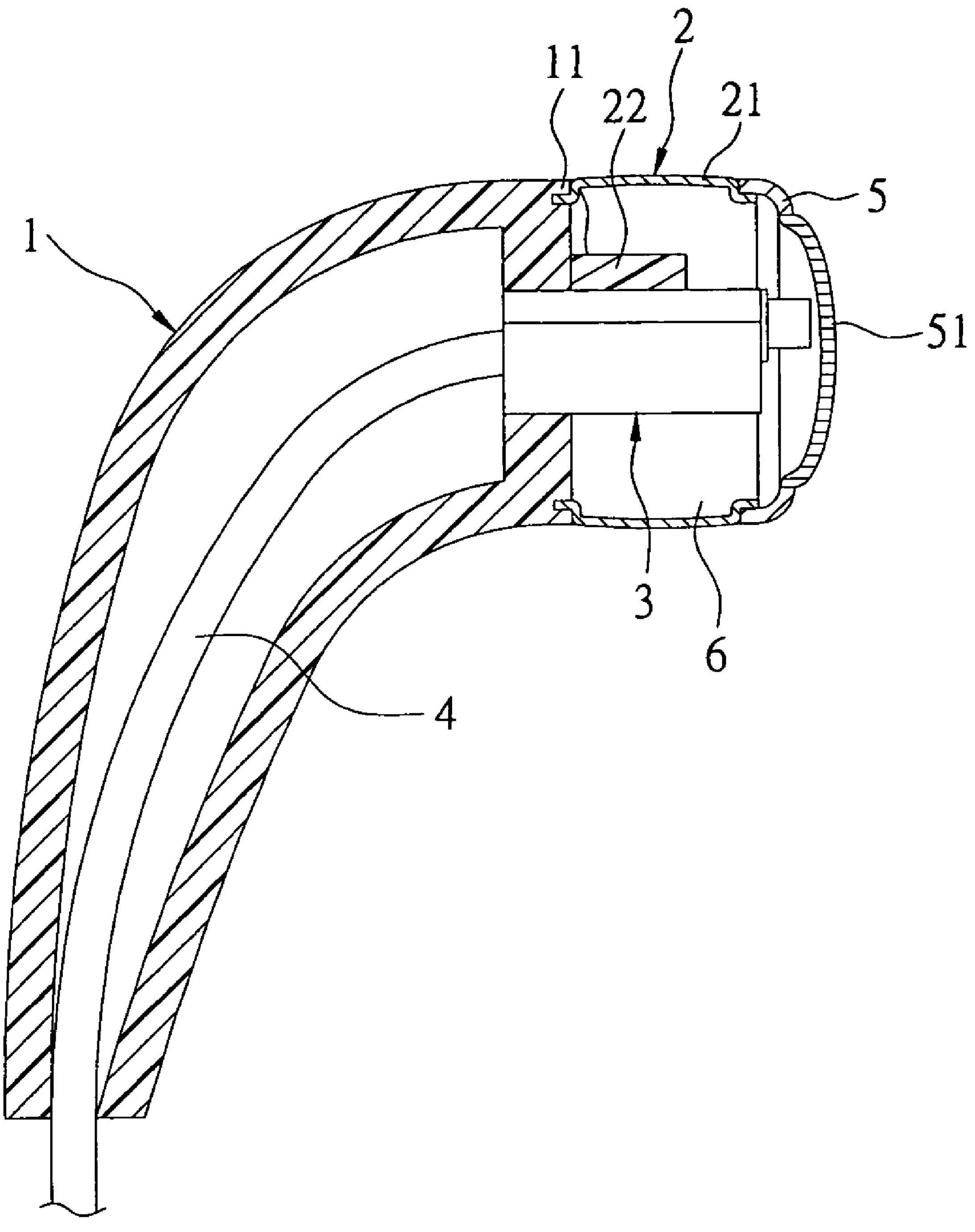
FIG. 3 is a sectional drawing showing an earphone device according to the present invention.

References are made to FIGS. 2 and 3. The present invention provides an earphone integrated with a microphone including a main body 1, a microphone unit 2, and a speaker unit 3. The main body 1 is a hollow housing made of plastic material, one end of which is formed as a connecting portion 11 for connecting the microphone 2 with the speaker unit 3.

The microphone unit 2 includes a sound-absorbing film 21 and a circuit unit 22. The sound absorbing-film 21 is a hollow column capable of being plugged into the user's ear canal, in tight contact with the inner wall thereof, and the rear end of the sound-absorbing film 21 is fixedly linked to the connecting portion 11 of the main body 1. The circuit unit 22 includes electronic elements such as transistors and capacitors (not shown). The circuit unit 22 is positioned inside the sound-absorbing film 21, properly fixed on the main body 1, and electrically connected to the sound-absorbing film 21 and also to a signal line 4. Another end of a signal line 4 penetrates through the main body 1 for being electrically connected to an electronic device such as a mobile phone. It is noted that in this embodiment, a wired earphone is illustrated, so the signal line 4 is included. If applied in a wireless earphone or Bluetooth earphone, then the signal line 4 is not needed. The sound-absorbing film 21 of the microphone unit 2 can be plugged into the ear canal of the user, is capable of sensing or receiving the vibration generated, and can absorb the signal and then transmit it the same to the circuit unit 22. The sound-absorbing film 21 adopts a contact sensing manner for sound absorption, blocking interference from the sound from the speaker unit 3. Furthermore, the front end of the sound-absorbing film 21 also can be connected to a cover 5, which has plural sound-holes 51 therein for outputting the sound of the speaker unit 3.

Figure 4:
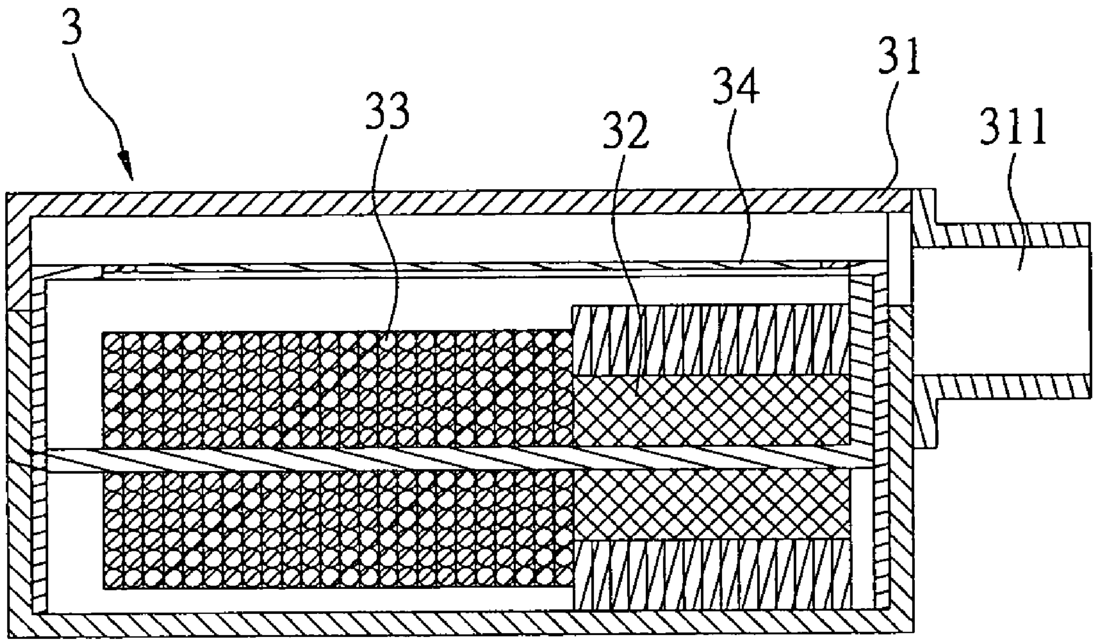
FIG. 4 is a sectional drawing showing a speaker unit of the earphone device according to the present invention.

The speaker unit 3 is mounted inside the sound-absorbing film 21 of the microphone unit 2 and is properly fixed on the main body 1. The speaker unit 3 is a miniature speaker including a housing 31, a permanent magnet 32, a coil 33 and a vibrating film 34, as shown in FIG. 4. The housing is a hollow housing made of a metal material and one end thereof has a sound-outputting hole 311, which faces the sound-holes 51 of the cover 5. The permanent magnet 32, the coil 33 and the vibrating film 34 are mounted inside the housing 31, the coil 33 is electrically connected to the vibrating film 34, and the coil 33 of the speaker unit 3 is also properly and electrically connected to the signal line 4. The coil 33 can promote the vibrating film 34 to sound through being driven by the signal current for converting the electronic signal of an electronic device, such as a mobile phone, into a sound that can be heard by a human ear. The vibrational direction of the vibrating film 34 is perpendicular to the sound-outputting hole 311 of the housing 31, such that the sound wave sent out by the vibrating film 34 can be reflected by the housing 31 and then sent out by the sound-outputting hole 311. This prevents the sound wave from being directly transmitted to the ear of the user and causing discomfort for the ear drum. Moreover, a sound-absorbing material 6 is mounted between the speaker unit 3 and the sound-absorbing film 21 of the microphone unit 2. The sound-absorbing material 6 is silica gel, by which a sound isolation area can be formed so that the speaker unit 3 does not interfere with the sound-absorbing film 21. Through the composition described above, the earphone device integrated with microphone can be achieved.

According to the present invention, the microphone unit 2 is integrated in the earphone device; namely, the microphone 2 is mounted on the peripheral of the speaker unit 3 of the earphone device, such that the earphone device may concurrently have an earphone and a microphone function. During use, the whole structure formed by the earphone and the microphone is fixedly assembled in the same position, for example, plugged in the ear canal of the user, so the assembly thereof is more convenient and the microphone is more stable, which facilitates sound reception.

Furthermore, the microphone 2 of the present invention does not need a clip to clip on the clothing worn by the user, so the whole structure can be simplified and the manufacturing cost can be reduced. Moreover, the microphone 2 is plugged in the ear canal of the user together with the earphone device, so it is not exposed. The appearance of the user is thus not influenced, and the activity of the user is not hindered, either.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An earphone device integrated with a microphone, comprising:

a main body;

a transcutaneous microphone unit connected to the main body, said transcutaneous microphone unit being operably coupled to an inner wall of a user's ear canal for receiving transcutaneously conducted soundwaves generated by the user speaking; and a speaker unit with a vibrating film mounted inside the transcutaneous microphone unit and provided with a sound-outputting hole;

wherein the transcutaneous microphone unit includes a sound absorbing film surrounding the speaker unit and separated therefrom by a space, a sound absorbing material filling the space between the sound absorbing film and the speaker unit, whereby the speaker unit and the transcutaneous microphone unit are integrated within the earphone device adjacent each to the other.

2. The earphone device according to claim 1, wherein one end of the main body is formed as a connecting portion, and the connecting portion is connected to the transcutaneous microphone unit.

3. The earphone device according to claim 1, wherein a front end of the transcutaneous microphone unit is connected to a cover and the cover has sound holes therein.

4. The earphone device according to claim 1, wherein the transcutaneous microphone unit comprises a circuit unit, the sound-absorbing film of the transcutaneous microphone unit being a hollow column and being connected to the main body through a rear end thereof, and the circuit unit being fixed on the main body and electrically connected to the sound-absorbing film.

5. The earphone device according to claim 4, wherein the circuit unit of the transcutaneous microphone unit is electrically connected to a signal line.

6. The earphone device according to claim 4, wherein the speaker unit is mounted inside the sound-absorbing film of the transcutaneous microphone unit.

7. The earphone device according to claim 1, wherein the speaker unit is a miniature speaker.

8. The earphone device according to claim 1, wherein the speaker unit at least comprises a housing, a permanent magnet, a coil and said vibrating film, the housing having said sound-outputting hole in one end thereof, the permanent magnet, the coil and the vibrating film being mounted inside the housing, the coil being electrically connected to the vibrating film and to a signal line, and the vibrating direction of the vibrating film being perpendicular to the sound-outputting hole of the housing.

9. The earphone device according to claim 1, wherein the sound absorbing material includes a silica gel material.

10. An earphone device integrated with a microphone, comprising:

a main body;

a transcutaneous microphone unit connected to the main body, said transcutaneous microphone unit being operably coupled to an inner wall of a user's ear canal for receiving transcutaneously conducted soundwaves generated by the user speaking; and a speaker unit with a vibrating film mounted inside the microphone unit and provided with a sound-outputting hole;

wherein the transcutaneous microphone unit includes a sound absorbing film surrounding the speaker unit with said vibrating film and separated therefrom by a space, the absorbing film being connected to the main body, the absorbing film adopts a contact sensing manner and is capable of sensing or receiving the vibration generated, absorbing the signal and then transmitting it to a circuit unit, a sound absorbing material filling the space between the sound absorbing film and the speaker unit, by which a sound isolation area can be formed so that the speaker unit does not interfere with the absorbing film.

* * * * *